United States Patent [19]
Turowski-Wanke et al.

[11] Patent Number: 5,998,354
[45] Date of Patent: Dec. 7, 1999

[54] FLOWABLE, AQUEOUS PEARLY LUSTER DISPERSION CONTAINING BEHENIC ACID AS PEARLESCENT COMPONENT AND LAURYL ETHER SULFATE AS DISPERSANT

[75] Inventors: Angelika Turowski-Wanke, Kelkheim; Peter Naumann, Taunusstein, both of Germany

[73] Assignee: Clariant GmbH, Frankfurt, Germany

[21] Appl. No.: 08/982,237

[22] Filed: Dec. 1, 1997

[30] Foreign Application Priority Data

Dec. 3, 1996 [DE] Germany .................. 196 50 089

[51] Int. Cl.$^6$ .................. C11D 1/04; C11D 1/28
[52] U.S. Cl. .................. 510/416; 510/426; 510/430; 510/437
[58] Field of Search .................. 424/70.31, 70.12, 424/70.19, 70.21, 70.24, 70.28; 510/125, 416, 122, 506, 124, 126, 128, 159, 505, 127, 119, 123, 426, 430, 437; 252/311, 357

[56] References Cited

U.S. PATENT DOCUMENTS

| | | | |
|---|---|---|---|
| 2,674,580 | 4/1954 | Henklin | 252/117 |
| 2,770,599 | 11/1956 | Henklin | 252/117 |
| 2,950,254 | 4/1960 | Meinhard et al. | 252/152 |
| 4,824,594 | 4/1989 | Hoeffkes et al. | 252/174.21 |
| 4,948,528 | 8/1990 | Hoeffkes et al. | 252/357 |
| 5,017,305 | 5/1991 | Hoeffkes et al. | 252/311 |
| 5,248,445 | 9/1993 | Rizvi et al. | 252/174.5 |
| 5,360,581 | 11/1994 | Rivzi et al. | 252/544 |
| 5,403,508 | 4/1995 | Reng et al. | 252/174.22 |
| 5,466,395 | 11/1995 | Tosaka et al. | 252/551 |
| 5,711,899 | 1/1998 | Kawa et al. | 252/311 |

OTHER PUBLICATIONS

McCutcheon's Emulsifiers and Detergents—1997.

*Primary Examiner*—Yogendra Gupta
*Assistant Examiner*—Gregory E. Webb
*Attorney, Agent, or Firm*—Miles B. Dearth

[57] ABSTRACT

The invention provides a flowable pearly luster concentrate comprising 5–30% of behenic acid formulated in an aqueous dispersion comprising 1–50% of $C_{12}$— to $C_{14}$— ether sulfates or acylisethionates and, if desired, from 0.1 to 10% of polyhydric alcohols. The composition according to the invention can be used in liquid surfactant formulations.

15 Claims, No Drawings

FLOWABLE, AQUEOUS PEARLY LUSTER DISPERSION CONTAINING BEHENIC ACID AS PEARLESCENT COMPONENT AND LAURYL ETHER SULFATE AS DISPERSANT

BACKGROUND OF THE INVENTION

Flowable, aqueous pearly luster dispersion containing behenic acid as pearlescent component and lauryl ether sulfate as dispersant This invention relates to a flowable or pumpable, aqueous pearly luster dispersion comprising 5–30% of pearlescent components.

In order to give surfactant formulations a better appearance and thus also a higher commercial value, pearly luster dispersions are often incorporated. Examples thereof include liquid washing and cleaning products (e.g. floor cleaners and dishwashing compositions) and liquid cosmetics preparations (e.g. body care and body cleansing products, shampoos, bath products, etc.). Pearly luster dispersions give the formulations a silky or mother-of-pearl-like appearance. The effect is produced by light scattering at the dispersed, mostly leaf-shaped crystals of the pearlescent components.

Pearly luster dispersions according to the prior art mainly comprise at least one pearlescent compound, at least one dispersant and water. Examples of pearlescent compounds are fatty acid monoalkanolamides, fatty acid dialkanolamides, monoesters or diesters of ethylene glycol or mixtures thereof, propylene glycol or its oligomers, mono- or diesters of alkylene glycols with fatty acids, fatty acids and their metal salts, monoesters or polyesters of glycerol with carboxylic acids and keto sulfones of various types.

Pearly luster concentrates based on the aforementioned pearlescents are known, for example, from DE-A-16 69 152, JP-56/71021 (Chem. Abstr. 95/156360), DE-A-34 11 328 and DE-A-35 19 081.

The concentrates known from these publications include fatty acid monoalkanolamides or fatty acid dialkanolamides as part of the pearlescent substances. However, alkanolamides and their derivatives are suspected of contributing to the formation of nitrosamines. It is therefore desired to formulate cosmetic preparations without such alkanolamides and alkanolamide derivatives.

Omitting the fatty acid alkanolamides from the known pearly luster concentrates does, however, lead to a marked reduction in the pearlescent properties. DE-37 24 547 has thus already proposed the use of essentially linear, saturated fatty acids, including inter alia behenic acid, as pearlescent substance.

EP-0 449 904 discloses that markedly higher concentrations of pearlescent substances must be used in order to obtain a satisfactory pearly luster in the final product. It also describes how pearly luster products based on fatty acids, their salts and their esters as the pearlescent component have only low thermal stability and become partially or completely dissolved at the usual use concentrations in surfactant formulations during storage. These disadvantages have meant that such systems have not become established on the market.

The object was therefore to develop a pearly luster product which does without fatty acid alkanolamides or fatty acid esters, has good stability on storage, and brings about a pearlescence effect which corresponds to the prior art.

SUMMARY OF THE INVENTION

Surprisingly, it has now been found that pearly luster concentrates comprising behenic acid as pearlescent component combined with an alkali metal salt of lauryl ether sulfate as dispersant lead to an excellent pearly luster effect within 1–5 days.

The invention accordingly provides a pearly luster dispersion comprising

A) 5–30% by weight of behenic acid and/or behenic acid salts

B1) 1 to 50% by weight of one or more compounds of the formula

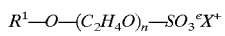

$$R^1-O-(C_2H_4O)_n-SO_3^-X^+$$

in which
  $R^1$ is $C_{12}$— to $C_{14}$—alkyl,
  n is 2 or 3, and
  $X^+$ is an alkali metal ion or an ammonium ion, or B2) 1 to 50% by weight of one or more compounds of the formula

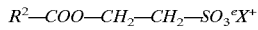

$$R^2-COO-CH_2-CH_2-SO_3^-X^+$$

in which
  $R^2$ is $C_8$— to $C_{18}$—alkyl,
  $X^+$ is an alkali metal ion or an ammonium ion, or B3) 1 to 50% by weight of a mixture of the substances specified under B1) and B2), and C) water and optionally other customary ingredients to 100% by weight.

DESCRIPTION OF THE PREFERRED EMBODIMENTS

X is preferably sodium or potassium, and n is preferably 2. 10 to 20% by weight of behenic acid are preferably used. The substances specified under B1) are preferably used in amounts of from more than 10 to 50% by weight, in particular from more than 10 to 30% by weight. The substances specified under B2) are preferably used in amounts of from 1 to 20% by weight, in particular from 2 to 16% by weight. Behenic acid salts which are preferably used are alkali metal and ammonium salts, in particular sodium and potassium salts.

The pearly luster dispersions according to the invention may include, as further customary ingredients, up to 10% by weight of polyhydric $C_2$— to $C_8$—alcohols. Preferred polyhydric alcohols are $C_2$— to $C_6$—polyols, in particular ethylene glycol, 1,2- and 1,3-propylene glycol, glycerol, di- and triethylene glycol, erythritol, arabitol, adonitol, xylitol, sorbitol, mannitol and dulcitol. If the pearly luster dispersions contain only a compound of the formula B1 the dispersion is preferably free of polyhydric $C_2$–$C_8$ alcohols. Examples of other customary ingredients include preservatives and buffers.

The aqueous pearly luster dispersions according to the invention are flowable and pumpable and can thus be used without difficulty in automatic pumping, metering and mixing equipment. They have the following advantages over the prior art dispersions:

they have better foaming behavior in the Ross-Miles test
  no glycol or ethylene glycol stearates or esters are used
  they can be prepared without alcohols
  they are free from nitrosable amines and alkanolamides
  they make lower demands on process control and apparatus during preparation the resulting pearly luster concentrates are of low viscosity and are thus very readily pumpable. The low viscosity also has a favorable effect on the hot/cold behavior.

The pearly luster dispersions according to the invention are preferably prepared by initially heating the water and dispersant to a temperature of from about 70° to about 90° C. in a mixing vessel (heatable tank). Separately, the behenic acid is melted in a second tank at a temperature of, generally, from about 70° to about 90° C. until homogeneous. The homogeneously molten behenic acid is introduced into the water/dispersant mixture at the stated temperature of from about 70° to about 90° C. with stirring. To heat-treat and homogenize the resulting dispersion, it is maintained at a temperature of about 70° to about 90° C. with stirring (about 15 to 30 minutes). Stirring is continued while the dispersion is cooled to a temperature of 25° C. in stages. The viscosity of the pearly luster concentrate is in most cases so low that it is not necessary to use special stirring equipment such as homogenizers or other high-speed mixing apparatus. The behenic acid crystallizes out during cooling, and the low-viscosity pearly luster concentrate can be drawn off at 25° C.

The pearly luster dispersions according to the invention are suitable for preparing pearlescent liquid, aqueous surfactant formulations. They can, for example, be incorporated into liquid light-duty detergents, universal detergents, manual dishwashing compositions, rinse aids, liquid cleaning products and disinfectants, liquid soaps, hair shampoos, hair conditioners, hair colorants, hair waving preparations, foam baths, face cleansers, shower preparations and 2 in 1 formulations. The pearly luster dispersions according to the invention enhance the conditioning effect of hair shampoos, in particular of the 2 in 1 shampoos which include water-soluble and/or water-insoluble dispersed agents, such as silicone derivatives (e.g. dimethicones).

The aqueous pearly luster dispersions according to the invention can be easily incorporated into the surfactant formulations while cold, as a result of which the latter acquire the desired pearlescence. The required amount of pearly luster dispersion is from 1 to 10% by weight, preferably from 2 to 5% by weight, based on the weight of the surfactant formulation to be treated. The pearly luster dispersion is added in the stated quantity to the surfactant formulations, preferably as the last component, at room temperature and with stirring. The pearly luster concentrate develops its luster and its richness in the formulation after approximately 1–5 days. The final products obtained thereafter have an excellent stable pearlescence.

The surfactant compositions in which the pearly luster dispersions according to the invention can be used are described below.

Suitable anionic surfactants include sulfonates, sulfates, carboxylates, phosphates and mixtures of said compounds. Suitable cations are alkali metals such as, for example, sodium or potassium, or alkaline earth metals such as, for example, calcium or magnesium, and ammonium, substituted ammonium compounds, including mono-, di- or triethanolammonium cations and mixtures of the cations. The following types of anionic surfactants are of particular interest: alkyl ester sulfonates, alkyl sulfates, alkyl ether sulfates, alkylbenzenesulfonates, secondary alkanesulfonates and soaps as described below.

Alkyl ester sulfonates include linear esters of $C_8$–$C_{20}$—carboxylic acids (i.e. fatty acids) which are sulfonated using gaseous $SO_3$, as described in The Journal of the American Oil Chemists Society 52 (1975), pp. 323–329. Suitable starting materials are natural fats such as, for example, tallow, palm oil or coconut oil, but they can also be synthetic. Preferred alkyl ester sulfonates, particularly for laundry detergent applications, are compounds of the formula

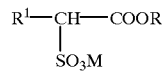

where $R^1$ is a $C_8$–$C_{20}$—hydrocarbon radical, preferably alkyl, and R is a $C_1$–$C_6$—hydrocarbon radical, preferably alkyl. M is a cation which forms a water-soluble salt with the alkyl ester sulfonate. Suitable cations are sodium, potassium, lithium or ammonium cations, such as monoethanolamine, diethanolamine and triethanolamine. $R^1$ is preferably $C_{10}$–$C_{16}$—alkyl and R is preferably methyl, ethyl or isopropyl. Particular preference is given to methyl ester sulfonates in which $R^1$ is $C_{10}$–$C_{16}$—alkyl.

Alkyl sulfates in this connection are water-soluble salts or acids of the formula $ROSO_3M$, where R is preferably a $C_{10}$–$C_{24}$—hydrocarbon radical, preferably $C_{10}$–$C_{20}$—alkyl or hydroxyalkyl, particularly preferably $C_{12}$–$C_{18}$—alkyl or hydroxyalkyl. M is hydrogen or a cation, e.g. an alkali metal cation (e.g. sodium, potassium, lithium), ammonium or substituted ammonium, e.g. methyl-, dimethyl- and trimethylammonium cations and quaternary ammonium cations, such as tetramethylammonium and dimethylpiperidinium cations and quaternary ammonium cations derived from alkylamines such as ethylamine, diethylamine, triethylamine and mixtures thereof. Alkyl chains with $C_{12}$–$C_{16}$ are preferred for low wash temperatures (e.g. below approximately 50° C.) and alkyl chains with $C_{16}$–$C_{18}$ are preferred for higher wash temperatures (e.g. above approximately 50° C.).

Alkyl ether sulfates are water-soluble salts or acids of the formula $RO(A)_mSO_3M$, where R is an unsubstituted $C_{10}$–$C_{24}$-alkyl or hydroxyalkyl radical, preferably a $C_{12}$–$C_{20}$-alkyl or hydroxyalkyl radical, particularly preferably $C_{12}$–$C_{18}$-alkyl or hydroxyalkyl radical. A is an ethoxy or propoxy unit, m is a number greater than 0, preferably between approximately 0.5 and approximately 6, particularly preferably between approximately 0.5 and approximately 3, and M is a hydrogen atom or a cation such as, for example, sodium, potassium, lithium, calcium, magnesium, ammonium or a substituted ammonium cation. Specific examples of substituted ammonium cations are methyl-, dimethyl-, trimethylammonium and quaternary ammonium cations such as tetramethylammonium and dimethylpiperidinium cations, and those which are derived from alkylamines, such as ethylamine, diethylamine, triethylamine and mixtures thereof. Examples which may be given are $C_{12}$–$C_{18}$ fatty alcohol ether sulfates where the content of ethylene oxide is 1, 2, 2.5, 3 or 4 mol per mole of fatty alcohol ether sulfate, and where M is sodium or potassium.

In secondary alkanesulfonates, the alkyl group can either be saturated or unsaturated, branched or linear and may be substituted by a hydroxyl group. The sulfo group can occupy any position over the whole carbon chain, except that the primary methyl groups at the start and end of the chain have no sulfo groups. The preferred secondary alkanesulfonates contain linear alkyl chains having from approximately 9 to 25 carbon atoms, preferably from approximately 10 to approximately 20 carbon atoms and particularly preferably from approximately 13 to 17 carbon atoms. Examples of the preferred cation are sodium, potassium, ammonium, mono-, di- or triethanolammonium, calcium or magnesium.

Other suitable anionic surfactants are alkenyl- or alkylbenzenesulfonates. The alkenyl or alkyl group can be branched or linear and may be substituted by a hydroxyl group. The preferred alkylbenzenesulfonates contain linear alkyl chains having from approximately 9 to 25 carbon atoms, preferably from approximately 10 to approximately 13 carbon atoms, and the cation is sodium, potassium, ammonium, mono-, di- or triethanolammonium, calcium or magnesium and mixtures thereof. For mild surfactant systems, magnesium is the preferred cation, while sodium is preferred for standard washing applications. The same applies to alkenylbenzenesulfonates.

The term anionic surfactants also includes olefinsulfonates which are obtained by sulfonation of $C_{12}-C_{24}$—, preferably $C_{14}-C_{16}$—, α-olefins with sulfur trioxide and subsequent neutralization. Owing to the preparation process, these olefinsulfonates may contain relatively small amounts of hydroxyalkanesulfonates and alkanedisulfonates. Specific mixtures of a-olefinsulfonates are described in U.S. Pat. No. 3,332,880.

Further preferred anionic surfactants are carboxylates, for example fatty acid soaps and comparable surfactants. The soaps can be saturated or unsaturated and can contain various substituents, such as hydroxyl groups or a-sulfonate groups. Linear saturated or unsaturated hydrocarbon radicals having from approximately 6 to approximately 30, preferably from approximately 10 to approximately 18 carbon atoms are preferably present.

Suitable anionic surfactants are also salts of acylamino carboxylic acids, the acylsarcosinates which are produced by reacting fatty acid chlorides with sodium sarcosinate in an alkaline medium; fatty acid-protein condensation products which are obtained by reacting fatty acid chlorides with oligopeptides; salts of alkylsulfamido carboxylic acids, salts of alkyl and alkylaryl ether carboxylic acids; $C_8-C_{24}$— olefinsulfonates, sulfonated polycarboxylic acids prepared by sulfonation of the pyrolysis products of alkaline earth metal citrates, as described for example in GB-1,082,179; alkyl glycerol sulfates, fatty acyl glycerol sulfates, alkylphenol ether sulfates, primary paraffinsulfonates, alkyl phosphates, alkyl ether phosphates, isethionates, such as acylisethionates, N-acyltaurides, alkyl- succinates, sulfosuccinates, monoesters of sulfosuccinates (particularly saturated and unsaturated $C_{12}-C_{18}$-monoesters) and diesters of sulfosuccinates (particularly saturated and unsaturated $C_{12}-C_{18}$-diesters), acylsarcosinates, sulfates of alkylpolysaccharides such as sulfates of alkyl polyglycosides, branched primary alkyl sulfates and alkylpolyethoxycarboxylates such as those of the formula $RO(CH_2CH_2)_kCH_2COO^{-M+}$, where R is $C_8-C_{22}$—alkyl, k is a number from 0 to 10 and M is a cation, resin acids or hydrogenated resin acids, such as rosin or hydrogenated rosin or tall oil resins and tall oil resin acids. Further examples are described in Surface Active Agents and Detergents (Vol. I and 11, Schwartz, Perry and Berch).

Examples of suitable nonionic surfactants are the following types:

Polyethylene, polypropylene and polybutylene oxide condensates of alkylphenols.

These compounds comprise the condensation products of alkylphenols having a $C_6-C_{20}$—alkyl group, which can be either linear or branched, with alkene oxides. Preference is given to compounds having approximately 5 to 25 mol of ethylene oxide per mole of alkylphenol. Commercially available surfactants of this type are, for example, Igepal® CO-630, Triton® X45, X-114, X-100 and X102, and the ®Arkopal-N grades from Hoechst AG.

Condensation products of aliphatic alcohols having from approximately 1 to approximately 25 mol of ethylene oxide.

The alkyl chain of the aliphatic alcohols can be linear or branched, primary or secondary, and generally contains from approximately 8 to approximately 22 carbon atoms. Particular preference is given to the condensation products of $C_{10}-C_{20}$—alcohols with from approximately 2 to approximately 18 mol of ethylene oxide per mole of alcohol. The alkyl chain can be saturated or else unsaturated. The alcohol ethoxylates can have a narrow ("narrow range ethoxylates") or a broad ("broad range ethoxylates") ethylene oxide homolog distribution. Examples of commercially obtainable nonionic surfactants of this type are Teritol® 15—S—9 (condensation product of a $C_{11}-C_{15}$ linear secondary alcohol with 9 mol of ethylene oxide), Tergitol® 24-L-NMW (condensation product of a $C_{12}-C_{14}$ linear primary alcohol with 6 mol of ethylene oxide, having a narrow molecular weight distribution). This product class also includes the Genapol® grades from Hoechst AG.

Condensation products of ethylene oxide with a hydrophobic base formed by condensation of propylene oxide with propylene glycol.

The hydrophobic moiety of these compounds preferably has a molecular weight of between approximately 1500 and approximately 1800. The addition of ethylene oxide to this hydrophobic part leads to an improvement in the solubility in water. The product is liquid up to a polyoxyethylene content of approximately 50% of the total weight of the condensation product, which corresponds to a condensation with up to approximately 40 mol of ethylene oxide. Commercially obtainable examples of this product class are the Pluronic® grades from BASF and the ®Genapol PF grades from Hoechst AG.

Condensation product of ethylene oxide with a reaction product of propylene oxide and ethylenediamine.

The hydrophobic unit of these compounds consists of the reaction product of ethylenediamine with excess propylene oxide and generally has a molecular weight of from approximately 2500 to approximately 3000. Ethylene oxide is added onto this hydrophobic unit until the product has a content of from approximately 40 to approximately 80% by weight of polyoxyethylene and a molecular weight of from approximately 5000 to approximately 11000. Commercially obtainable examples of this compound class are the ®Tetronic grades from BASF and the ®Genapol PN grades from Hoechst AG.

Semipolar nonionic surfactants

This special category of nonionic compounds includes water-soluble amine oxides, water-soluble phosphine oxides and water-soluble sulfoxides, each having an alkyl radical of approximately 10 to approximately 18 carbon atoms. Semipolar nonionic surfactants are also amine oxides of the formula

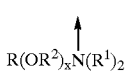

where R is an alkyl, hydroxyalkyl or alkylphenyl group each having from approximately 8 to approximately 22 carbon atoms, $R^2$ is an alkylene or hydroxyalkylene group having from approximately 2 to 3 carbon atoms or mixtures thereof, each radical $R^1$ is an alkyl or hydroxyalkyl group having from approximately 1 to approximately 3 carbon atoms, or a polyethylene oxide group having from approximately 1 to approximately 3 ethylene oxide units. The $R^1$ groups can be linked to one another via an oxygen or nitrogen atom and can therefore form a ring. Amine oxides of this type are, in particular, $C_{10}$–$C_{18}$—alkyldimethylamine oxides and $C_8$–$C_{12}$—alkoxyethyldihydroxyethylamine oxides.

Fatty acid amides

Fatty acid amides have the formula

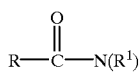

where R is an alkyl group having from approximately 7 to approximately 21, preferably from approximately 9 to approximately 17, carbon atoms, and each $R^1$ radical is hydrogen, $C_1$–$C_4$—alkyl, $C_1$–$C_4$—hydroxyalkyl or $(C_2H_4O)_xH$, where x varies from approximately 1 to approximately 3. Preference is given to $C_8$–$C_{20}$amides, monoethanolamides, diethanolamides and isopropanolamides.

Further suitable nonionic surfactants are, in particular, alkyl and alkenyl oligoglycosides and also fatty acid polyglycol esters or fatty amine polyglycol esters having in each case from 8 to 20, preferably from 12 to 18, carbon atoms in the fatty alkyl radical, alkoxylated triglycamides, mixed ethers or mixed formals, fatty acid N-alkylglucamides, protein hydrolyzates, phosphine oxides or dialkyl sulfoxides Typical examples of amphoteric and zwitterionic surfactants are alkyl betaines, alkylamide betaines, aminopropionates, aminoglycinates, or amphoteric imidazolinium compounds of the formula

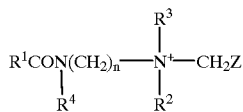

in which $R^1$ is $C_8$–$C_{22}$—alkyl or —alkenyl, $R^2$ is hydrogen or $CH_2CO_2M$, $R^3$ is $CH_2CH_2OH$ or $CH_2CH_2OCH_2CH_2COOM$, $R^4$ is hydrogen, $CH_2CH_2OH$ or $CH_2CH_2COOM$, Z is $CO_2M$ or $CH_2CO2M$, n is 2 or 3, preferably 2, M is hydrogen or a cation such as alkali metal, alkaline earth metal, ammonia or alkanolammonium.

Preferred amphoteric surfactants of this formula are monocarboxylates and dicarboxylates. Examples thereof are cocoamphocarboxypropionate, cocoamidocarboxypropionic acid, cocoamphocarboxyglycinate (also called cocoamphodiacetate) and cocoamphoacetate.

Other preferred amphoteric surfactants are alkyldimethyl betaines and alkyldipolyethoxy betaines with an alkyl radical, which can be linear or branched, having from approximately 8 to approximately 22 carbon atoms, preferably having from 8 to 18 carbon atoms and particularly preferably having from approximately 12 to approximately 18 carbon atoms. These compounds are marketed, for example, by Hoechst AG under the trade name ®Genagen LAB.

The cationic surfactants used are quaternary ammonium salts of the type

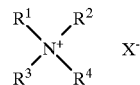

in which
$R^1$=$C_8$–$C_{24}$—n— or isoalkyl, preferably $C_{10}$–$C_{18}$—n—alkyl
$R^2$=$C_1$–$C_4$—alkyl, preferably methyl
$R^3$=$R^1$ or $R^2$
$R^4$=$R^2$ or hydroxyethyl or hydroxypropyl or their oligomers
$X^-$=a suitable anion.

Examples thereof are distearyidimethylammonium chloride, ditallow-alkyldimethylammonium chloride, ditallow-alkylmethylhydroxypropyl-ammonium chloride, cetyltrimethylammonium chloride or the corresponding benzyl derivatives, such as dodecyidimethylbenzylammonium chloride. Cyclic quaternary ammonium salts, such as alkylmorpholine derivatives, can also be used.

In addition to the quaternary ammonium compounds, it is also possible to use imidazolinium compounds (1) and imidazoline derivatives (2).

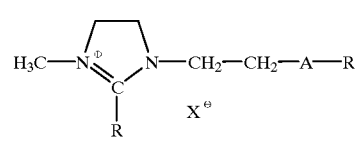

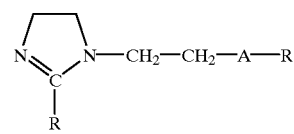

in which
R=$C_8$–$C_{24}$—n— or iso-alkyl, preferably $C_{10}$–$C_{18}$—n—alkyl
x=bromide, chloride, iodide, methosulfate
A=—NH—CO—, —CO—NH—, —O—CO—, —CO—O—.

Ester quats are further suitable cationic surfactants. These are reaction products of alkanolamines and fatty acids, which have been subsequently quaternized with customary alkylating or hydroxyalkylating agents.

Preferred alkanolamines are compounds of the formula

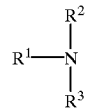

where
$R^1$=$C_1$–$C_3$—hydroxyalkyl, preferably hydroxyethyl and
$R^2$, $R^3$=independently of one another, $R^1$ or $C_1$–$C_3$—alkyl, preferably methyl.

Triethanolamine and methyidiethanolamine are particularly preferred.

Further particularly preferred starting products for ester quats are aminoglycerol derivatives such as, for example, dimethylaminopropanediol.

Alkylating or hydroxyalkylating agents are alkyl halides, preferably methyl chloride, dimethyl sulfate, ethylene oxide and propylene oxide.

Examples of ester quats are compounds of the formulae:

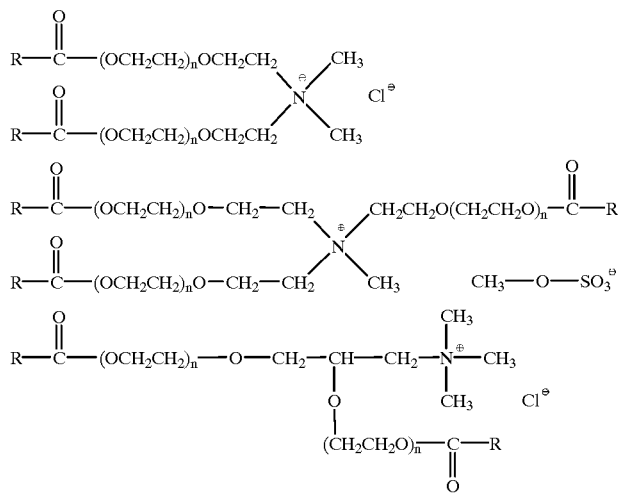

where R—C—O is derived from $C_8$–$C_{24}$ fatty acids which can be saturated or unsaturated. Examples thereof are caproic acid, caprylic acid, hydrogenated, nonhydrogenated or partially hydrogenated tallow fatty acids, stearic acid, oleic acid, linolenic acid, behenic acid, palmitostearic acid, myristic acid and elaidic acid. n is in the range from 0 to 10, preferably 0 to 3, particularly preferably 0 to 1.

EXAMPLES

The pearly luster dispersions according to the invention are described in the following examples. The quantities are given in percent by weight. The pearly luster dispersions were prepared according to the aforementioned method. The resulting aqueous dispersions were tested for their flow behavior after 3 days and for their pearly luster in a shampoo formulation. Both tests were carried out purely visually, comparing with commercial products. The test results are given in the following table.

Euperlano® PK 3000 from Henkel was used as the comparative example (called "Comparison" in the table). It was incorporated at a concentration of 5% into a shampoo formulation, as was also the case for the examples according to the invention in the table.

Euperlano® PK 3000 is a pearly luster agent comprising monoglycol mono- and distearate as pearlescent components. It further includes alkylamidopropyl betaine, alcohol ethoxylates and sodium chloride.

The quantity data for the commercial products in the following Tables I and 11 are based on pure substances, and not on the commercially available dilute solutions.

TABLE I

| Exp. No. | Composition | Mixing sequence | 5% in shampoo, 4° C., evaluation | 5% in shampoo, 25° C., evaluation | 5% in shampoo, 45° C., evaluation | Concentrate (3 days) |
|---|---|---|---|---|---|---|
| NG 160/96 | 4% SCID 12% Genapol LRO 14% stearic acid | SCID, water, LRO to 90° C., add acid melt | Clear solution (1) | 2 phases (1) | Slightly cloudy solution (1) | Solid |
| NG 162/96 | 4% SCID 12% Genapol LRO 7% each of stearic/ palmitic acid | SCID, water, LRO to 90° C., add acid melt | Clear solution (1) | 2 phases (1) | Clear solution (1) | Solid |
| NG 163/96 | 4% SCID 12% Genapol LRO 14% palmitic acid | SCID, water, LRO to 90° C., add acid melt | Clear solution (1) | Clear liquid + solid particles (1) | Clear solution (1) | Solid |
| NG 165/96 according to the invention | 4% SCID 12% Genapol LRO 14% behenic acid | SCID, water, LRO to 90° C., add acid melt | Milky, slight PL (2–3) | As analogous comparison (5) | Slight PL, glassy (2–3) | Liquid |
| NG 166/96 | 4% SCID 12% Genapol LRO 14% arachidic acid | SCID, water, LRO to 90° C., add acid melt | Milky solution (2) | PL close to comparison (4) | Clear solution (1) | Liquid |
| NG 175/96 | 4% SCID 14% behenic acid 12% Gen. CAB | SCID + water + CAB + benzoate, 90° C./behenic acid melt | | Cloudy, slight PL (2–3) | | Liquid |

TABLE I-continued

| Exp. No. | Composition | Mixing sequence | 5% in shampoo, 4° C., evaluation | 5% in shampoo, 25° C., evaluation | 5% in shampoo, 45° C., evaluation | Concentrate (3 days) |
|---|---|---|---|---|---|---|
| NG 176/96 | 0.45% Na benzoate 4% SCID 14% behenic acid 12% Plantaren 2000 | SCID + water + CAB + benzoate, 90° C./behenic acid melt | | Milky cloudiness (2) | | Thixotropic |
| NG 177/96 | 0.45% Na benzoate 4% SCID 14% behenic acid 12% Plantaren 2000 | SCID + water + CAB + benzoate, 90° C./behenic acid melt | | Milky cloudiness (2) | | Liquid |
| NG 178/96 | 0.45% Na benzoate 4% SCID 14% behenic acid 12% Gen. UD 50 | SCID + water + CAB + benzoate, 90° C./behenic acid melt | | Distinct PL (3–4) | | Viscous |
| NG 180/96 | 0.45% Na benzoate 4% SCID 14% behenic acid 12% Hostacerin DGL | SCID + water + DGL + benzoate, 90° C./behenic acid melt | | Slight PL (2–3) | | Creamy |
| NG 181/96 | 0.45% Na benzoate 4% SCID 14% behenic acid 12% Gen. C 100 | SCID + water + CAB + benzoate, 90° C./behenic acid melt | | Cloudy, slight PL (2–3) | | Creamy |
| NG 182/96 | 0.45% Na benzoate 4% SCID 14% behenic acid 6% Gen. C 100 6% Hostacerin DGL | SCID + water + mixture + benzoate, 90° C./behenic acid melt | | Cloudy, PL (3) | | Viscous |
| NG 184/96 | 4% SCID 14% behenic acid 6% Plantaren 1200 6% Gen. C 100 0.45% Na benzoate | SCID + water + mixture + benzoate, 90° C./behenic acid melt | | PL (3) | | Liquid |

TABLE II

| Exp. No. | % Genapol LRO | % Behenic acid (85%) | % SCID | PL | Viscosity at 20° C. (mPas), 7th week |
|---|---|---|---|---|---|
| NG 2/97 | 12 | 14 | 1 | 4–5 | 1530 |
| NG 3/97 | 12 | 14 | 2 | 5 | 1740 |
| NG 4/97 | 12 | 14 | 3 | 5 | 1850 |
| NG 6/97 | 14 | 14 | 1 | 4–5 | 1250 |
| NG 7/97 | 14 | 14 | 2 | 5 | 1110 |
| NG 12/97 | 16 | 14 | 1 | 4–5 | 1760 |
| NG 15/97 | 16 | 14 | 2 | 5 | 19800 |
| NG 16/97 | 16 | 14 | 3 | 5 | 18000 (35 days) |
| NG 20/97 | 18 | 14 | 1 | 4 | 20000 |
| NG 33/97 | 20 | 14 | 1 | 3 | 18000 (35 days) |
| NG 43/97 | 12 | 16 | 1 | 4 | 6250 |
| NG 44/97 | 12 | 16 | 2 | 4 | 5550 |
| NG 45/97 | 12 | 16 | 3 | 4 | 7800 |

Pearlescence ratings
1=Clear solution
2=Cloudy, no pearlescence
3=Slight pearlescence
4=Pearlescence close to comparison
5=Pearlescence same as comparison
Gen. CAB=Genapolo CAB=alkylamidopropyl betaine (30%) Gen. UD 50=Genapolo UD 050=C11-oxo alcohol polyglycol ether

+5 EO

Gen. C 100=Genapol® C100=C10/18 fatty alcohol polyglycol ether

+10 EO

Genapol LRO=28% alkyl ether sulfate, sodium salt in water
Hostacerin® DGL=ethoxylated fatty acid polyglycerol ester
Plantarene 1200 and 2000=alkyl polyglycosides from Henkel SCID=Hostapon® SCID=acylisethionate
PL=pearlescence

We claim:

1. A homogeneous, flowable or pumpable liquid pearly luster dispersion comprising
   (A) 5–30% by weight of behenic acid and/or behenic acid alkali metal or ammonium salts
   (B1) 1 to 50% by weight of one or more compounds of the formula

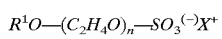
   $$R^1O-(C_2H_4O)_n-SO_3^{(-)}X^+$$

in which
   $R^1$ is $C_{12}$— to $C_4$—alkyl
   n is 2 or 3, and
   $X^+$ is an alkali metal ion or ammonium ion, and
   (B2) 1 to 50% by weight of one or more compounds of the formula

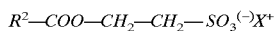
   $$R^2-COO-CH_2-CH_2-SO_3^{(-)}X^+$$

in which
   $R^2$ is $C_8$— to $C_{18}$—alkyl,
   $X^+$ is an alkali metal ion or ammonium ion, and
   C) water and optionally other customary ingredients to 100% by weight.

2. A pearly luster dispersion as claimed in claim 1 wherein n =2.

3. A pearly luster dispersion as claimed in claim 1 wherein X is sodium or potassium.

4. A pearly luster dispersion as claimed in claim 1, wherein 10 to 20% by weight of behenic acid are used.

5. A pearly luster dispersion as claimed in claim 1, wherein the compounds specified under BI) and B2) are present therein independently of one another in amounts of from 1 to 20% by weight.

6. A pearly luster dispersion according to claim 1 which is free of $C_2$–$C_8$—polyhydric alcohols and which contains more than 10 to 50% by weight of a compound B1.

7. A pearl luster dispersion according to claim 1 which is free of $C_2$–$C_8$—polyhydric alcohols and which contains more than 10 to 30% by weight of a compound B1.

8. A pearly luster dispersion as claimed in claim 1, which comprises preservatives and/or buffers.

9. A pearly luster dispersion as claimed in claim 1, which comprises up to 10% by weight of polyhydric $C_2$— to $C_8$—alcohols.

10. A pearly luster dispersion as claimed in claim 9, wherein polyhydric $C_2$— to $C_6$— alcohols are used.

11. A pearly luster dispersion as claimed in claim 9, wherein the polyhydric alcohols used are ethylene glycol, 1,2-propylene glycol, 1,3-propylene glycol, glycerol, diethylene glycol, triethylene glycol, erythritol, arabitol, adonitol, xylitol, sorbitol, mannitol, dulcitol or mixtures thereof.

12. A surfactant formulation comprising from 1 to 10% by weight of a pearly luster dispersion as claimed in one or more of claims 1 to 11.

13. A liquid light-duty detergent, universal detergent, manual dishwashing composition, rinse aid, liquid cleanser and disinfectant, liquid soap, hair shampoo, hair conditioner, hair colorant, hair waving preparation, foam bath, facial cleanser, shower preparation or 2 in 1 formulation, each of which comprises a pearly luster dispersion as claimed in one or more of claims 1 to 11.

14. The pearly luster dispersion of claim 5 wherein said B1) and B2) are present independently of one another in amount of from 2 to 16% by weight.

15. A homogeneous, flowable or pumpable liquid pearly luster dispersion containing no fatty acid alkanolamide or fatty acid ester, comprising
(A) 5–30% by weight of behenic acid and/or behenic acid alkali metal or ammonium salts
(B1) 1 to 50% by weight of one or more compounds of the formula

in which
$R^1$ is $C_{12}$— to $C_{14}$—alkyl
n is 2 or 3, and
$X^+$ is an alkali metal ion or ammonium ion, and
(B2) 1 to 50% by weight of one or more compounds of the formula

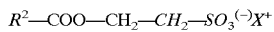

in which
$R^2$ is $C_8$— to $C_{18}$—alkyl,
$X^+$ is an alkali metal ion or ammonium ion, and
C) water and optionally other customary ingredients to 100% by weight.

* * * * *